(12) United States Patent
Pekrul et al.

(10) Patent No.: US 12,070,336 B2
(45) Date of Patent: Aug. 27, 2024

(54) HANDHELD STYLUS AND BASE AND METHODS OF USE

(71) Applicant: Ceraxis Health, Inc., Cleveland, OH (US)

(72) Inventors: Christopher Pekrul, Boston, MA (US); Scott Kokones, Brookline, MA (US); Omar Ansari, San Francisco, CA (US); Eugina Chun, San Francisco, CA (US); Brian Hoffer, San Francisco, CA (US); John Lai, San Francisco, CA (US); Adam Little, San Francisco, CA (US); David Lubensky, San Francisco, CA (US)

(73) Assignee: CERAXIS HEALTH, INC., Cleveland, OH (US)

( * ) Notice: Subject to any disclaimer, the term of this patent is extended or adjusted under 35 U.S.C. 154(b) by 0 days.

(21) Appl. No.: 18/466,560

(22) Filed: Sep. 13, 2023

(65) Prior Publication Data

US 2023/0414179 A1   Dec. 28, 2023

Related U.S. Application Data

(63) Continuation of application No. 17/155,991, filed on Jan. 22, 2021, now Pat. No. 11,793,464.

(Continued)

(51) Int. Cl.
*A61B 5/00* (2006.01)
*A61B 5/11* (2006.01)
(Continued)

(52) U.S. Cl.
CPC .......... *A61B 5/6897* (2013.01); *A61B 5/0004* (2013.01); *A61B 5/1101* (2013.01);
(Continued)

(58) Field of Classification Search
None
See application file for complete search history.

(56) References Cited

U.S. PATENT DOCUMENTS 9,186,095 B2 * 11/2015 Machado ................. A61B 5/11
10,028,695 B2   7/2018 Machado et al.
(Continued)

FOREIGN PATENT DOCUMENTS

KR   10-2018-0128127   12/2018
WO   WO 2014/043239 A2   3/2014

OTHER PUBLICATIONS

Examination Report mailed Oct. 20, 2023 in European Application No. 21711070.9 (6 pages).
(Continued)

*Primary Examiner* — Stephen T. Reed
(74) *Attorney, Agent, or Firm* — Finnegan, Henderson, Farabow, Garrett & Dunner, LLP

(57) ABSTRACT

The present disclosure provides methods and devices for assessing movement. In some exemplary embodiments, a system for assessing movement is provided. In some embodiments, the system includes a handheld device. In some embodiments, the handheld device includes a plurality of sensors configured to record motion and position data, a body having a plurality of sides, a battery, and a proximal end configured to interact with a touchscreen of a computing device.

19 Claims, 17 Drawing Sheets

Related U.S. Application Data

(60) Provisional application No. 62/964,360, filed on Jan. 22, 2020.

(51) Int. Cl.
    *G06F 3/01*           (2006.01)
    *G06F 3/0346*      (2013.01)
    *G06F 3/0354*      (2013.01)
    *G06F 3/038*       (2013.01)
    *G06F 3/039*       (2013.01)
    *G06F 3/044*       (2006.01)
    *H02J 7/02*         (2016.01)

(52) U.S. Cl.
CPC .......... *A61B 5/4082* (2013.01); *A61B 5/7445* (2013.01); *A61B 5/7455* (2013.01); *A61B 5/7475* (2013.01); *G06F 3/016* (2013.01); *G06F 3/0346* (2013.01); *G06F 3/03545* (2013.01); *G06F 3/038* (2013.01); *G06F 3/039* (2013.01); *G06F 3/044* (2013.01); *H02J 7/02* (2013.01); *A61B 2560/0214* (2013.01); *A61B 2560/0456* (2013.01); *A61B 2562/0219* (2013.01); *A61B 2562/0223* (2013.01); *G06F 2203/0384* (2013.01)

(56) References Cited

U.S. PATENT DOCUMENTS

| | | | |
|---|---|---|---|
| 2004/0140962 A1* | 7/2004 | Wang | G06F 3/03545 345/179 |
| 2014/0267147 A1* | 9/2014 | Buelow | G06F 3/03545 345/174 |
| 2016/0091993 A1* | 3/2016 | Pedersen | G06F 3/04162 345/179 |
| 2016/0128621 A1 | 5/2016 | Machado et al. | |
| 2021/0034188 A1* | 2/2021 | Kwon | G06F 3/03545 |

OTHER PUBLICATIONS

International Search report and Written Opinion mailed May 21, 2021 in International Application No. PCT/US2021/014726 (12 pages).

* cited by examiner

HANDHELD STYLUS AND BASE AND METHODS OF USE

CROSS-REFERENCE TO RELATED APPLICATION

This application is a continuation of U.S. patent application Ser. No. 17/155,991, filed Jan. 22, 2021, which claims the benefit of priority of U.S. Provisional Patent Application No. 62/964,360, filed Jan. 22, 2020, each of which is incorporated herein by reference in its entirety in the present application.

TECHNICAL FIELD

The present disclosure relates to devices and systems for assessing movement and corresponding methods of use.

BACKGROUND

Movement disorders may be described as a broad set of neurological diseases or conditions characterized primarily by abnormal movement of an affected individual. Such movement can either manifest via tremor or be slower, faster, or less smooth than the movement of a healthy individual. The assessment of movement disorders is traditionally done with subjective tests through numerous pieces of analog equipment. Increased adoption of handheld, wearable, and mobile technology provides an opportunity to streamline traditional assessments, provide more robust detail and data, and provide new metrics that are beneficial and desirable for clinicians and researchers in the treatment of neurological disorders.

SUMMARY

According to an exemplary embodiment of the present disclosure, a system for assessing movement is provided. In some embodiments, the system includes a handheld device. In some embodiments, the handheld device includes a plurality of sensors configured to record motion and position data. In some embodiments, the handheld device includes a body having a plurality of sides. In some embodiments, the handheld device includes a battery. In some embodiments, the handheld device includes a proximal end configured to interact with a touchscreen of a computing device. In some embodiments, the handheld device includes a button at a distal end.

According to an exemplary embodiment of the present disclosure, a method of assessing movement is provided. In some embodiments, the method includes administering a pre-determined task to a patient via a handheld device and a base. In some embodiments, the handheld device includes a plurality of sensors configured to record motion and position data, a body comprising a plurality of sides, a battery, and a proximal end configured to interact with a touchscreen of a computing device. In some embodiments, the base includes at least one sensor and a battery. In some embodiments, the method further includes transmitting data from the handheld device to the computing device. In some embodiments, the method further includes calculating, by the computing device, a performance score using an algorithm and data received from the handheld device. In some embodiments, the method further includes outputting, by the computing device, the performance score. In some embodiments, the method further includes determining, by the computing device, a treatment for the patient using the performance score.

Additional disclosure of the disclosed embodiments will be set forth in part in the description that follows.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain exemplary principles of certain disclosed embodiments as set forth in the accompanying claims.

DETAILED DESCRIPTION

Figure 1:
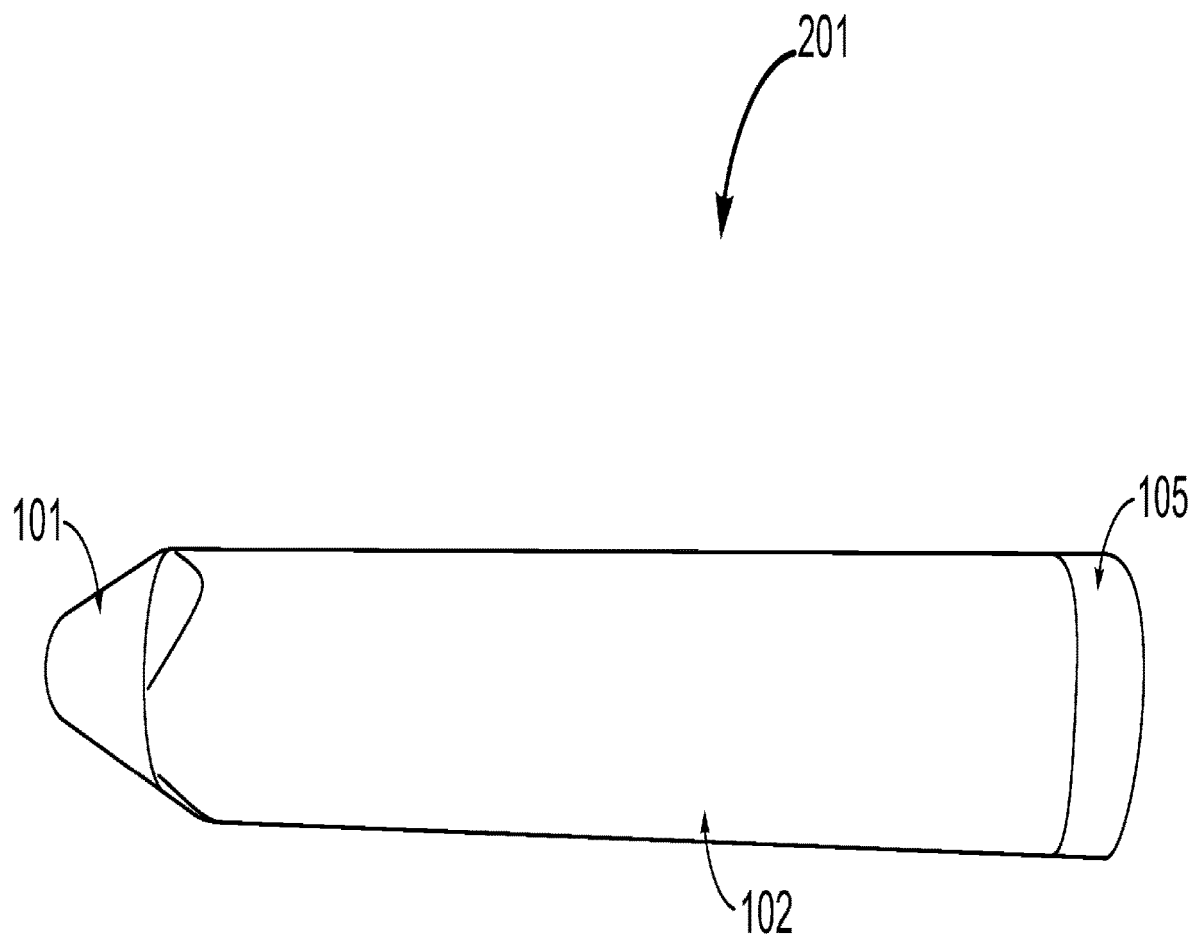
FIG. 1 depicts a side view of an exemplary stylus, according to some embodiments of the present disclosure.

Reference will now be made in detail to embodiments and aspects of the present disclosure, examples of which are illustrated in the accompanying drawings. Where possible, the same reference numbers will be used throughout the drawings to refer to the same or like parts.

The present disclosure provides a stylus configured to track movement of a user through one or more sensors. In some embodiments, the one or more sensors are configured to detect motion and position of the stylus. In some embodiments, the one or more sensors are configured to record data indicative of the motion and position of the stylus. In some embodiments, the recorded motion and position data are processed and analysis for assessing movement of the user. In some embodiments, the user is an individual or a patient having one or more disorders, diseases, and conditions. Such disorders, diseases, and conditions include, but not limited to, movement disorders (including but not limited to Parkinson's, Essential Tremor, Dystonia, Tourette's and Progressive Supranuclear Palsy), autism, heart failure, heart disease, traumatic brain injury, stroke, vestibular disease, migraines, dementia, amyotrophic lateral sclerosis (ALS), and attention deficit disorder (ADD).

In some embodiments, the stylus is a handheld device. In some embodiments, the one or more sensors include an accelerometer, a gyroscope, a force sensor, or a magnetometer. In some embodiments, one or more sensors are internal to the stylus. In some embodiments, one or more sensors are located on the external surface of the stylus. In some embodiments, one or more sensors are in the proximal end of the stylus. In some embodiments, one or more sensors are in the distal end of the stylus. In some embodiments, one or more sensors are located on one or more sides of the body of the stylus.

In some embodiments, the stylus is configured to assess movement disorder of the user based on the interaction between the stylus held by the user and one or more computing devices, such as a computing device having a capacitive touchscreen. In some embodiments, the interaction is between the stylus and a specific part of the user, such as one or more finger tips, a chin, or a nose. In some embodiments, the interaction is performed according to a predetermined task for the user.

The present disclosure further provides a base. The stylus consistent with embodiments of the present disclosure may interact with the base. In some embodiments, the base includes one or more hardware components, such as one or more sensors, a wireless charger for the stylus, a battery, a power supply cord, a computer-readable storage medium, a wireless communication module, and a processor. The wireless communication module is configured to wirelessly communicate with the stylus. In some embodiments, the wireless communication module is a communication circuit on the processor. The one or more sensors in the base may include at least one of an accelerometer, a gyroscope, a force sensor, a hall effect sensor, a capacitive sensor, a photoelectric sensor, an ultrasonic sensor, an infrared sensor, or a magnetometer.

Figure 2:
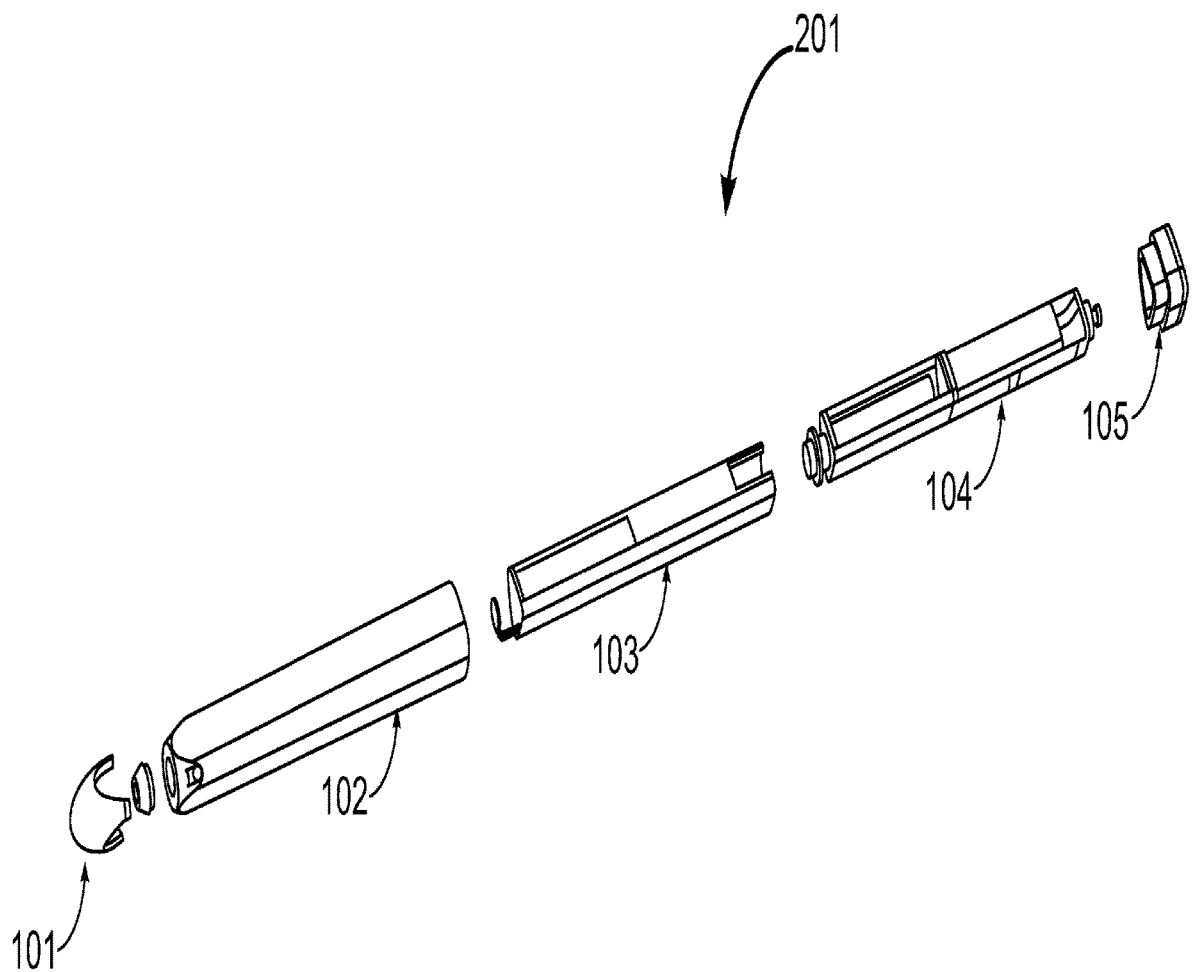
FIG. 2 depicts an exploded view of an exemplary stylus, according to some embodiments of the present disclosure.
Figure 3:
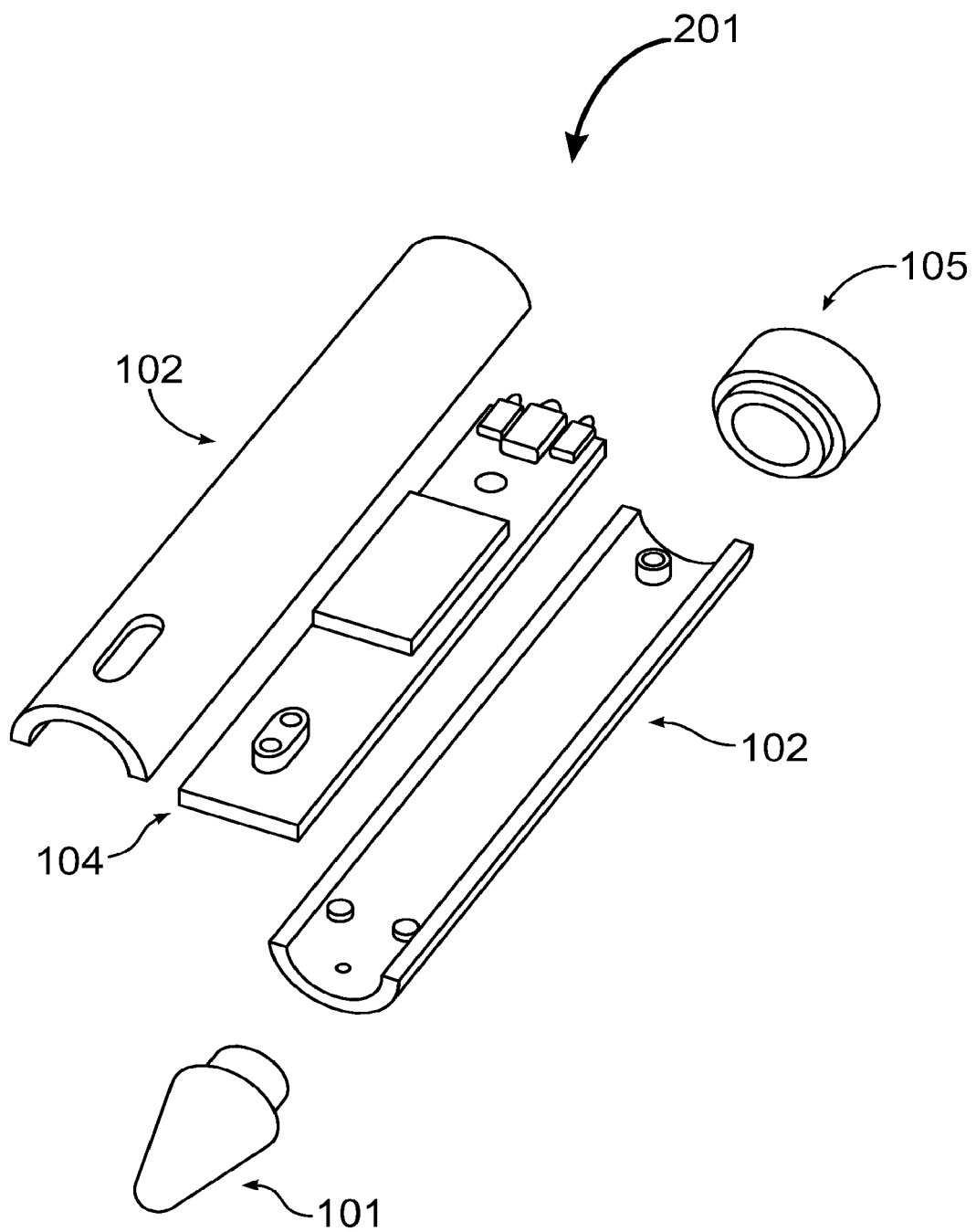
FIG. 3 depicts an exploded view of an exemplary stylus, according to some embodiments of the present disclosure.
Figure 4:
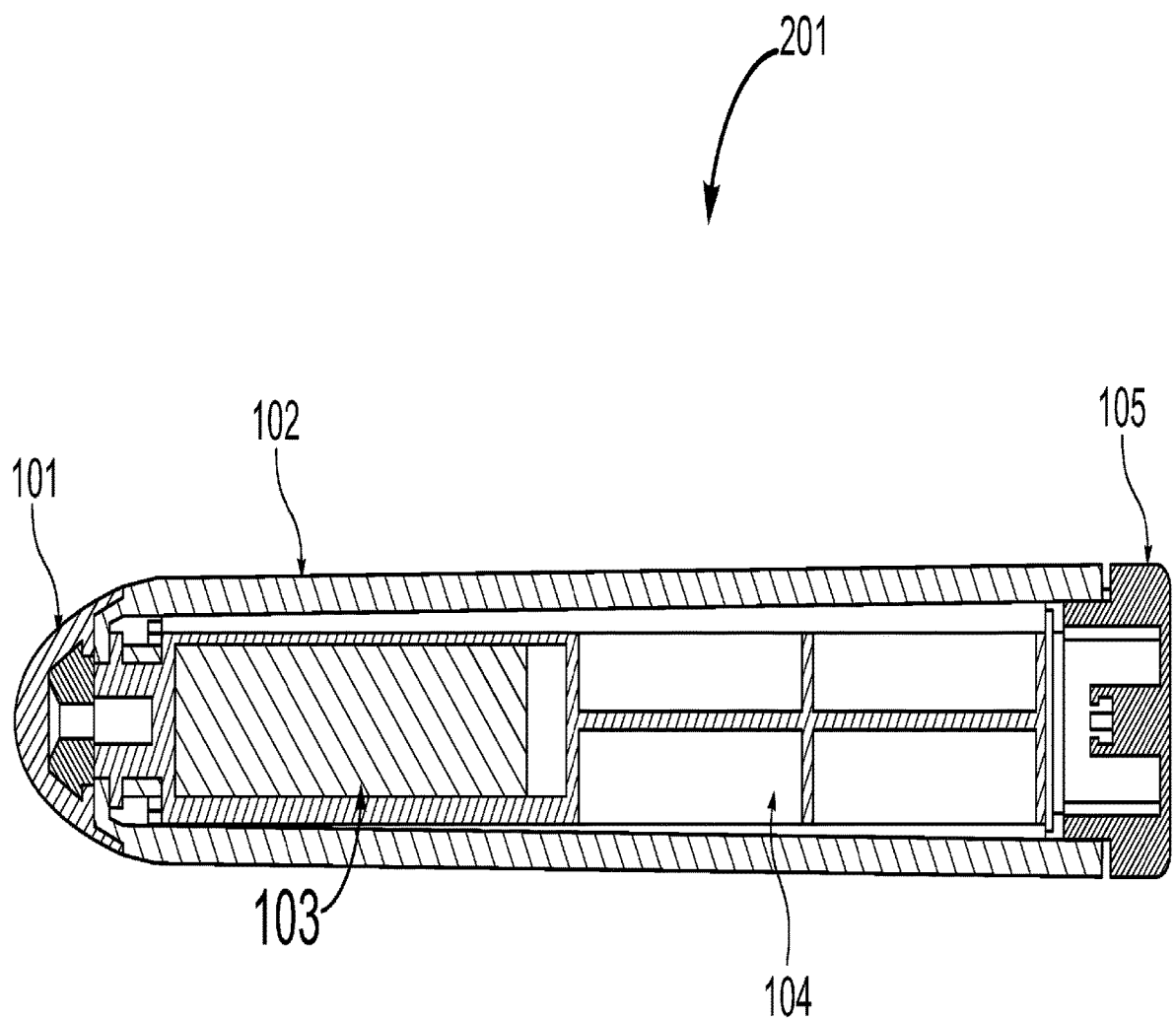
FIG. 4 depicts a longitudinal cross-sectional view of an exemplary stylus, according to some embodiments of the present disclosure.

FIG. 1 depicts a side view of an exemplary stylus (201), according to some embodiments of the present disclosure. FIG. 2 depicts an exploded view of an exemplary stylus (201), according to some embodiments of the present disclosure. FIG. 3 depicts another exploded view of an exemplary stylus (201), according to some embodiments of the present disclosure. FIG. 4 depicts a longitudinal cross-sectional view of an exemplary stylus (201), according to some embodiments of the present disclosure. As shown in FIGS. 1-4, in some embodiments, the stylus (201) includes multiple sections, including a first end or a distal end, a body (102), and a second end or a proximal end. In some embodiments, the first end includes a distal tip (101). In some embodiments, the distal tip (101) is configured to interact with a computing device, such as a tablet, a computer, a phone, or an iPad®. The body (102) is configured to be held in a hand by a user. In some embodiments, the body (102) provides tactile feedback to the user while the user is performing a task or during an assessment of the user's movement. In some embodiments, the tactile feel can be produced through any suitable mechanical and electrical device, such as a piezoelectric haptic feedback device, in the body (102). In some embodiments, the stylus (201) is configured to work with a base (202) as described in detail further below.

Figure 5:
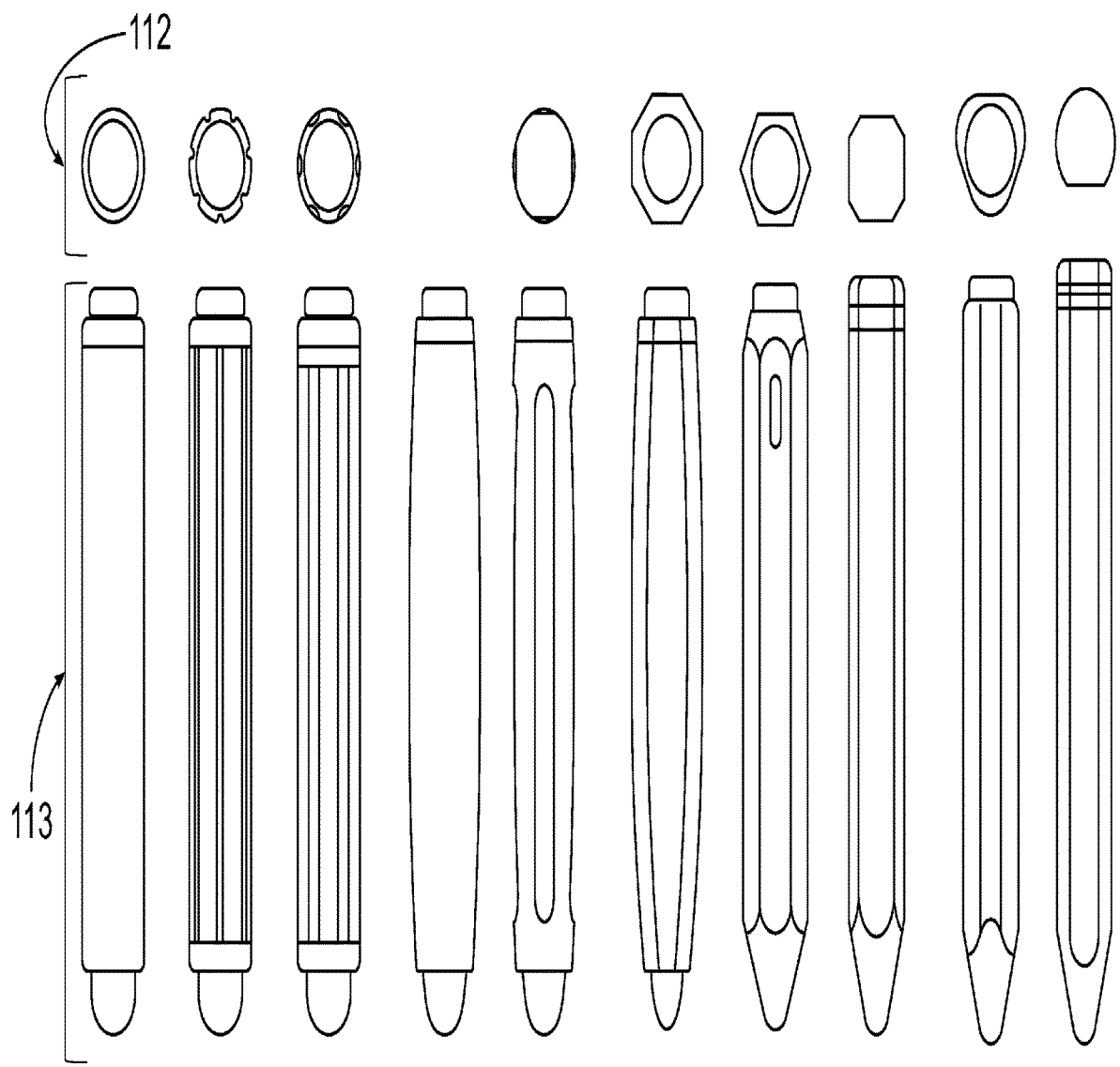
FIG. 5 depicts cross-sectional views and side views of various designs of an exemplary stylus, according to some embodiments of the present disclosure.

FIG. 5 depicts top views and side views of various designs of an exemplary stylus (201), according to some embodiments of the present disclosure. As illustrated in FIG. 5, the body (102) of the stylus (201) may have various cross-section designs including but not limited to a circle, triangle, square, oval, pentagon, and other symmetrical and non-symmetrical shapes. In some embodiments, the cross-section of the body (102) has a plurality of sides. In some embodiments, the cross-section of the stylus body (102) has an odd number of sides. FIG. 5 shows various configurations of the number of sides of the stylus (201) in a cross-sectional (112) view and in a side (113) view.

Figure 12:
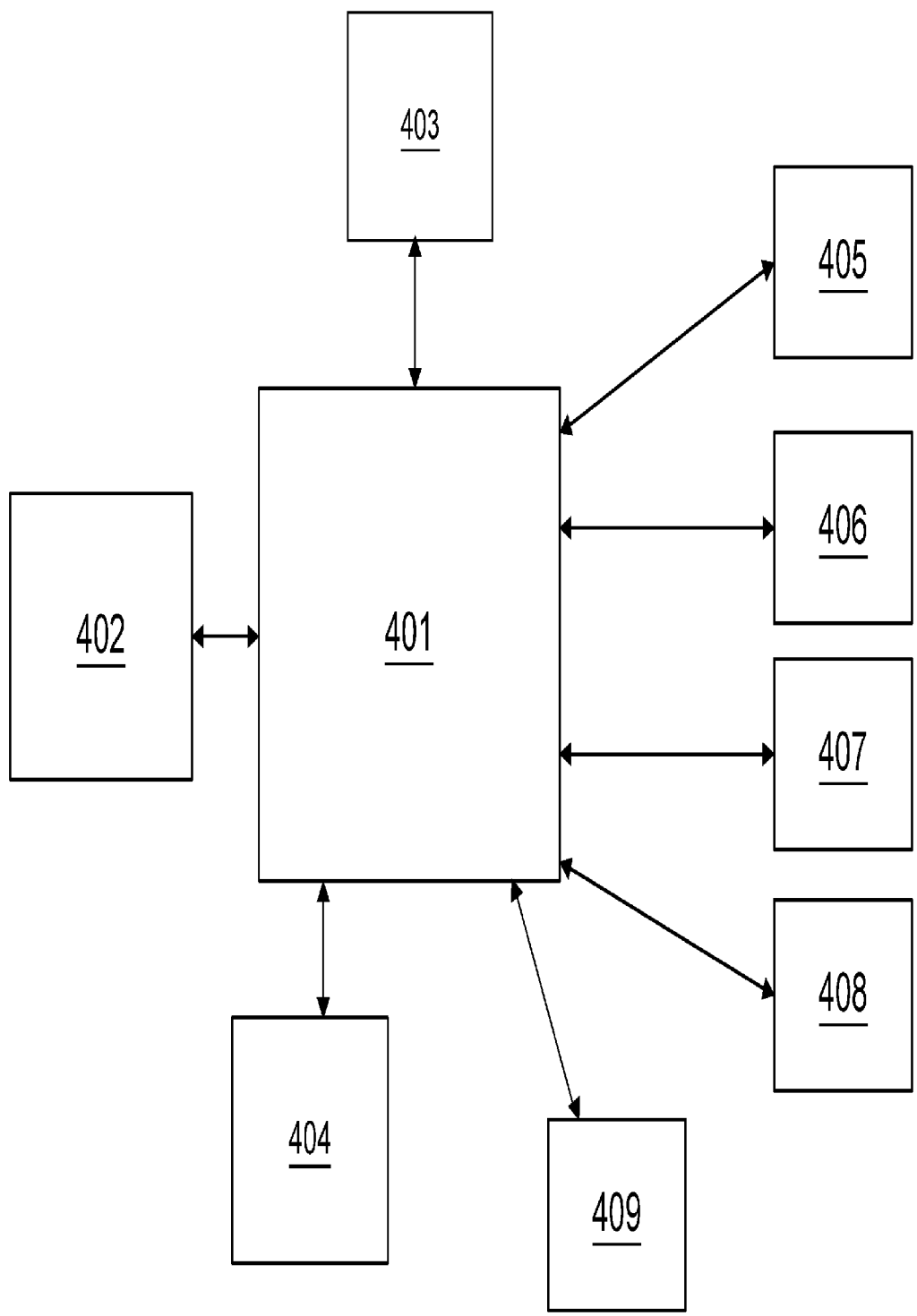
FIG. 12 depicts a schematic of exemplary electronic components within an exemplary stylus, according to some embodiments of the present disclosure.

In some embodiments, the body (102) is configured to receive one or more electronic components (104), such as processors, control circuits, signal processing circuits, and sensors (see also FIG. 12). In some embodiments, as shown in FIG. 2, the body (102) is configured to receive one or more batteries (103). In some embodiments, the body (102) is configured to receive a battery module including a recharging circuit for recharging the batteries (103). In some embodiments, as shown in FIGS. 2-4, the one or more electronic components (104) include one or more sensors. The one or more sensors include, but not limited to, an accelerometer, a gyroscope, a force sensor, a hall effect sensor, a capacitive sensor, a photoelectric sensor, an ultrasonic sensor, an infrared sensor, a pressure sensor, and a magnetometer (see also FIG. 12). In some embodiments, one or more of the sensors of the stylus (201) are in the proximal end of the stylus (201). In some embodiments, one or more of the sensors of the stylus (201) are in the distal end of the stylus. In some embodiments, one or more of the sensors of the stylus (201) are located on one or more sides of the body (201).

The body (102) of the stylus (201) may be made of any suitable materials, including, but not limited to, conductive materials, such as certain metals or plastics. The types of metal which may be used includes, but not limited to, one or more of aluminum, steel, stainless steel, copper, zinc, magnesium, or other alloys of the aforementioned metals. The types of plastics that may be used includes polyethylene terephthalate, high-density polyethylene, polyvinyl chloride, low-density polyethylene, polypropylene, polystyrene, polycarbonate, polyctide, acrylic, acrylonitrile, butadiene, styrene, fiberglass, nylon, or a combination thereof. In some embodiments, the body (102) is coated with one or more materials to enhance touch or feel for ergonomic reasons. In some embodiments, the body (102) is coated with one or more conductive materials to help with registering the touch of the stylus (201) held in a hand on a touchscreen, such as an iPad® or iPhone® screen, or other types of capacitive touch devices.

Figure 6:
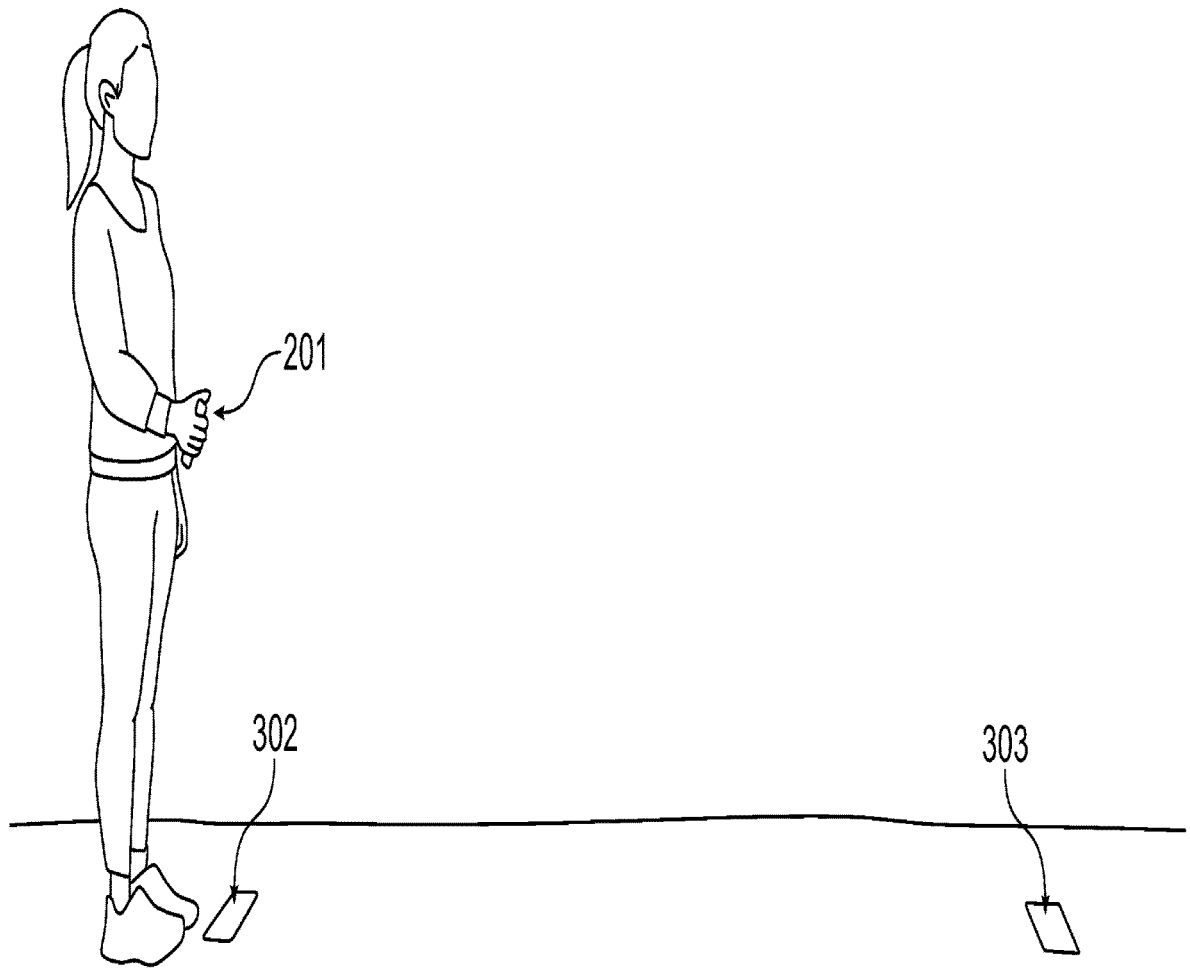
FIG. 6 depicts a user performing a gait task while holding an exemplary stylus, according to some embodiments of the present disclosure.
Figure 7:
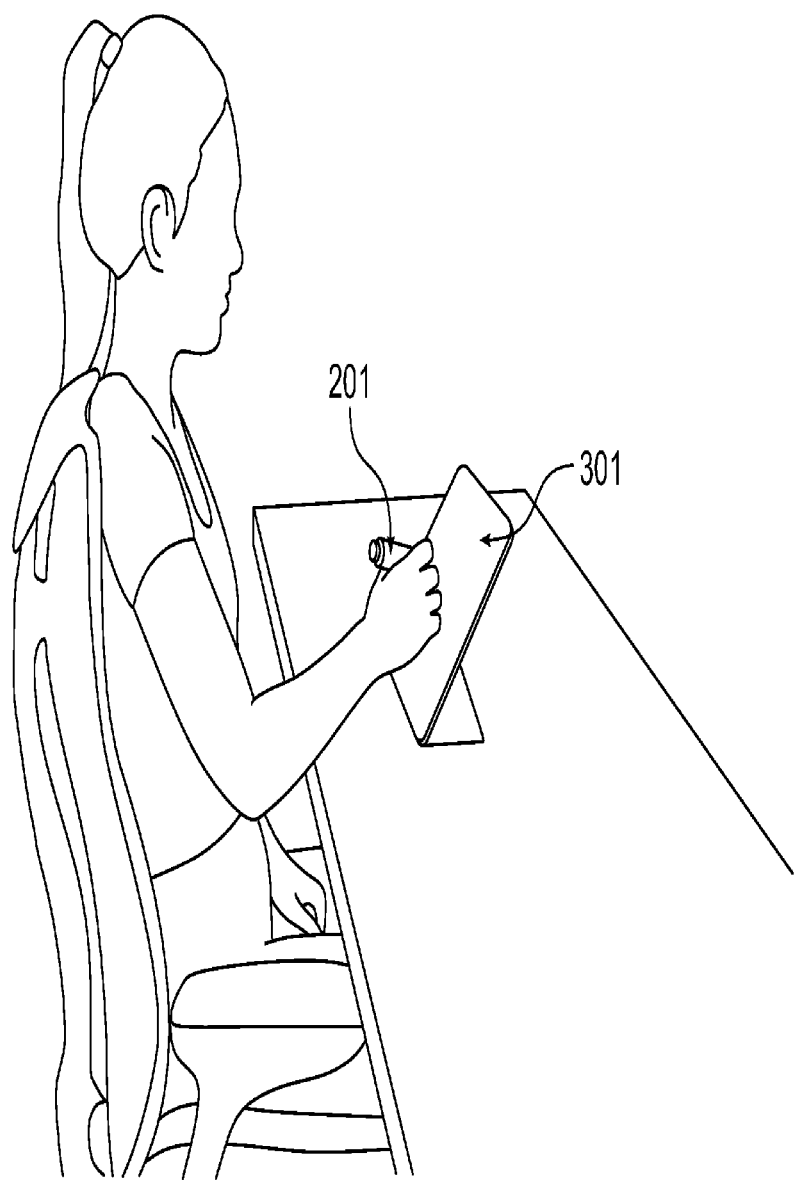
FIG. 7 depicts a user performing a task by using an exemplary stylus to interact with an exemplary computing device, according to some embodiments of the present disclosure.
Figure 8:
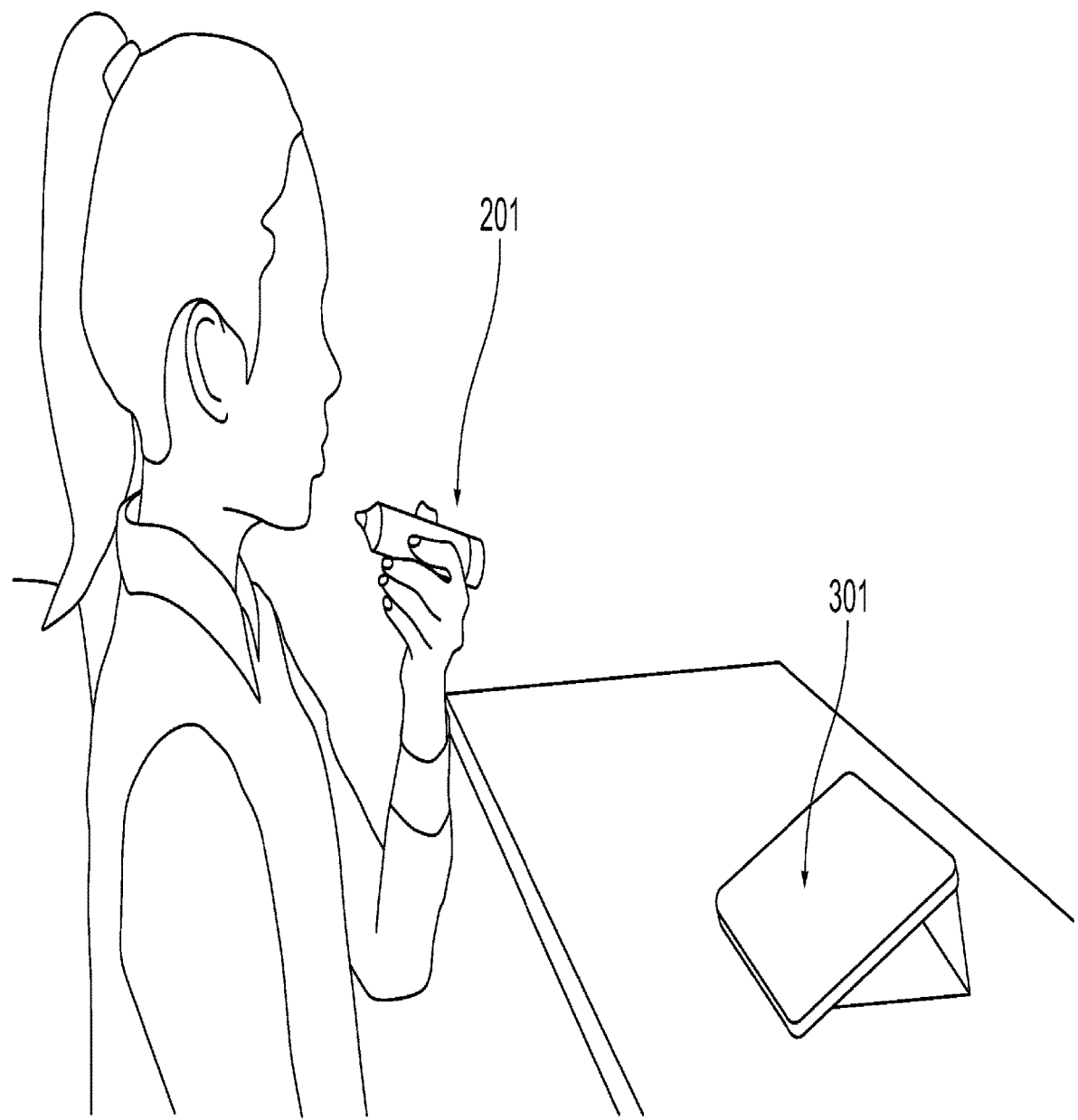
FIG. 8 depicts a user performing a task using an exemplary stylus, according to some embodiments of the present disclosure and a tablet.

The stylus (201) consistent with embodiments with the present disclosure may be handheld (see FIGS. 6-11), affixed to an individual via a clip, positioned in an individual's pocket, or affixed to an individual via a strap or any other suitable way. The stylus (201) consistent with embodiments with the present disclosure provides a device for performing a self-administered assessment of human movement. In some embodiments, the stylus (201) is used for administration of pre-determined tasks for the assessment of individuals with various disorders, diseases, and conditions. Such conditions include movement disorders (including but not limited to Parkinson's, Essential Tremor, Dystonia, Tourette's and Progressive Supranuclear Palsy), autism, heart failure, heart disease, traumatic brain injury, stroke, vestibular disease, migraines, dementia, amyotrophic lateral sclerosis (ALS), and attention deficit disorder (ADD). In some embodiments, the stylus (201) is used for the assessment of movement as it relates to treatment with deep-brain stimulation (DBS) therapies, assessment of fall risk, assessment of frailty, assessment of pharmaceuticals and the assessment of various psychological disorders. In some embodiments, the stylus (201) is used for administrating pre-determined tasks assessing action tremor, resting tremor, postural tremor, gait, balance, or a tapping test. For example, the stylus (201) is used for administrating a gait task. In some embodiments, the gait task is a timed 25-foot walk or a timed 10-meter walk from a first point (302) to a second point (303) (see FIG. 6). In other embodiments, the gait task is a Time Up-and-Go task, 5-time sit-to-stand task, or tandem gait task.

According to some embodiments of the present disclosure, the stylus (201) is used for the assessment of human movement. In some embodiments, movement is detected and/or tracked by capturing data via sensors of the stylus (201). In some embodiments, movement is detected or tracked by measuring or tracking the interaction of the stylus (201) with a touchscreen of an external computing device (301) (see FIG. 7). In some embodiments, movement is detected or tracked by both capturing data via one or more of the sensors of the stylus (201) and measuring or tracking the interaction between the stylus (201) with the touchscreen of a computing device. In some embodiments, movement is detected or tracked by both capturing data via one or more sensors of the stylus (201) and measuring or tracking the interaction between the stylus (201) with a specific part of an individual, such as a chin or nose (see FIG. 8).

In some embodiments, movement and/or position data is captured during execution of a pre-determined task by an individual by capturing data via one or more sensors of the stylus (201) and measuring or tracking the interaction of the stylus with a touchscreen of an external computing device (301). In some embodiments, movement and/or position data is captured during execution of a pre-determined task by an individual by capturing data via one or more of the sensors of the stylus (201) and measuring or tracking the interaction between the stylus (201) with the touchscreen of a computing device. In some embodiments, movement and/or data is captured during execution of a pre-determined task by an individual by capturing data via the one or more of the sensors of the stylus (201) and measuring or tracking the interaction between the stylus (201) with a specific part of an individual, such as a chin or nose.

Figure 11:
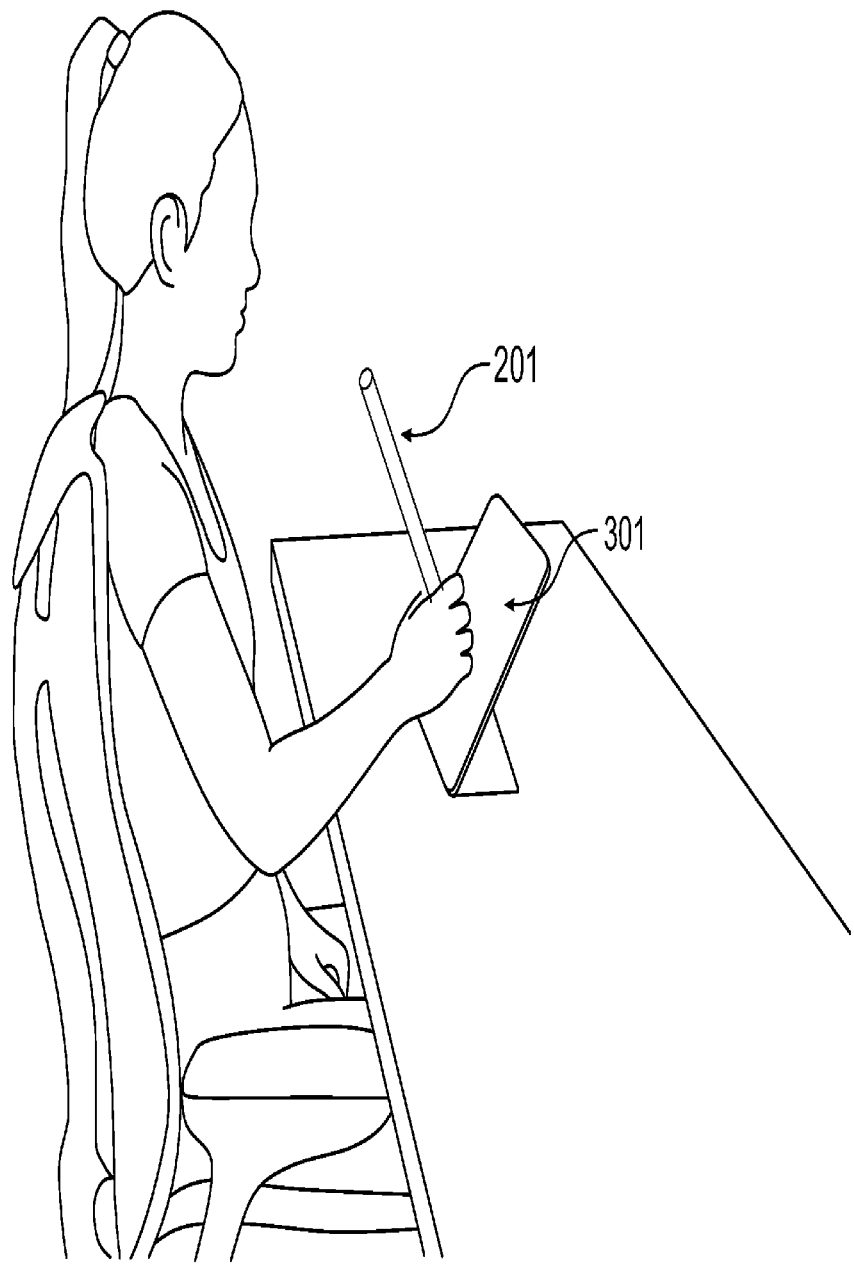
FIG. 11 depicts a user using an exemplary stylus contacting a touchscreen of a computing device, according to some embodiments of the present disclosure.

In some embodiments, the stylus (201) interacts with a touchscreen of an external computing device (301) by means of a tip (101) configured for contacting the touchscreen (see FIG. 11). In some embodiments, the tip (101) is a capacitive tip. In some embodiments, the interaction occurs during a task or an assessment requiring an individual to move the stylus (201) while keeping the tip (101) in contact with the touchscreen in accordance with a pre-determined path, to make contact with pre-determined targets presented on the touchscreen, or to hold the stylus tip at a single location on the touchscreen. In some embodiments, the stylus (201) is used by an individual to perform a task or an assessment during which the stylus (201) interacts with a specific part of an individual. Such an assessment may include a task wherein an individual, while holding the stylus (201), contacts the tip (101) of the stylus with a touchscreen device or a non-touchscreen surface, moves the stylus tip (101) towards the individual, contacts the tip (101) of the stylus to the individual's nose or chin, and returns to the original position. Such a task may be repeated for a plurality of times over a duration of time. In some embodiments, such an assessment is used to evaluate the symptoms of an individual with a movement disorder or other conditions. In some embodiments, such an assessment is used to prescribe or revise treatment of an individual through prescribing or modifying medication type, dose, therapy, or a combination thereof.

In certain embodiments, multiple stylus devices may be used for an assessment or a test. These types of assessments or tests may include tremor measurement where a patient's hands are held directly out in front of them with their arms straight and a stylus (201) held in each hand so tremor can simultaneously be measure from both hands. Other assessments or tests may include walking tests where a stylus (201) is held in each hand to help distinguish walking patterns, asymmetry, and other factors associated with gait.

In some embodiments, the stylus (201) may be used to evaluate a patient's balance through a balance test, during which a patient may hold the stylus (201). Examples of a balance test include standing on a stable surface with a two foot stance, standing on a stable surface with a single foot stance, standing on a padded surface with a two foot stance, standing on a padded surface with a single foot stance, standing on a dynamic surface with a two foot stance, and standing on a dynamic surface with a single foot stance.

FIG. 12 depicts a schematic of exemplary electronic components within an exemplary stylus (201), according to some embodiments of the present disclosure. As shown in FIG. 12, in some embodiments, the stylus (201) includes a processor (401) and a plurality of sensors. In some embodiments, the processor (401) includes one or more circuits, including, but not limited to, control circuits, signal processing circuits, logic circuits, communication circuits, and input/output circuits. In some embodiments, the processor has a sampling rate of 25 Hz to 100 Hz. In some embodiments, circuits of the processor (401) are configured to perform sensor polling, digital signal processing, and calibration processing. In some embodiments, the stylus (201) includes a volatile or a non-volatile computer-readable storage medium (402) configured to store computer program instructions and a memory (403). The computer program instructions stored in the computer-readable storage medium (402) can be read into memory (403) and executed by the processor (401) of the stylus (201) to perform various processing and control functions.

In some embodiments, as shown in FIG. 12, the plurality of sensors of the stylus (201) includes an accelerometer (405), a gyroscope (406), a force sensor (407), a pressure sensor (408), and a magnetometer (409). In some embodiments, the stylus (201) includes an inertial measure unit (IMU) (not shown). In some embodiments, the IMU includes an accelerometer, a gyroscope, and a magnetometer. In some embodiments, the IMU is a component of the processor (401).

In certain embodiments, the accelerometer (405) has three axis measurement, from about 12-bit to about 32-bit resolution, and ±1 g to ±8 g range. In some embodiments, the accelerometer (405) has three axis measurement, 13-bit resolution and ±2 g range. In certain embodiments, the gyroscope (406) has three axis measurement, sensitivity of at least about 14.375 LSBs per °/sec, from about 12-bit to about 32-bit resolution, and from about 60°/sec to about 1000°/sec range. In some embodiments, the gyroscope (406) has three axis measurement, a sensitivity of at least about 14.375 LSBs per °/sec, about 16-bit resolution, and ±200°/sec range. In certain embodiments, the magnetometer (409) has three axis measurement, from about 12-bit to about 32-bit resolution, and ±8 Gauss Fields range. In some embodiments, the magnetometer (409) has three axis measurement, about 12-bit resolution, and ±8 Gauss Fields range.

In certain embodiments, the tip (101) of the stylus is on a spring-loaded dowel that can displace. In certain embodiments, the tip (101) of the stylus may displace up to 20 millimeters. In some embodiments, the tip (101) of the stylus may displace up to 10 millimeters. In certain embodiments, the stylus is able to monitor the force exerted on the tip (101) through a force sensor, a piezoelectric force sensor, a linear potentiometer, an ultrasonic sensor, an optical sensor, a pressure sensor, or a strain gauge. In certain embodiments, the tip (101) is able to measure force from about 200 grams to about 10 kilograms. In some embodiments, the tip (101) is able to measure force of about 2 kilograms. In some embodiments, the tip (101) is able to measure displacement from about 0 millimeters to about 20 millimeters.

The stylus (201) may communicate with an external device via a communication module (404). In some embodiments, the communication module (404) includes a Bluetooth Low Energy (BLE) radio, such as an iBeacon or an iBeacon-compatible hardware transmitter configured to communicate with external devices, such as a mobile touchscreen device (e.g., iPhone® or iPad® from Apple Inc.) or the base (202). In some embodiments, the communication module (404) of the stylus (201) includes a wireless communication circuit that uses WiFi, ZigBee, or other proprietary wireless communication protocol. Additionally or alternatively, the communication module (404) of the stylus (201) may communicate with an external device via a wired connection. In some embodiments, the stylus (201) caches or otherwise stores data on the device itself, such as in the non-volatile computer-readable storage medium (402). In some embodiments, the stylus (201) offloads or transmits the stored data via packets to the base (202) or an external device, such as computing device (301). Examples of a non-volatile computer-readable storage medium include, but are not limited to, a phase-change random access memory (PRAM), a static random access memory (SRAM), a dynamic random access memory (DRAM), other types of random access memories (RAMs), a read-only memory (ROM), an electrically erasable programmable read-only memory (EEPROM), a flash memory or other memory technologies, a cache, a register, or any other non-transitory media that may be used to store information capable of being accessed by a processor.

In certain embodiments, the stylus (201) has one or more onboard batteries (103) and charging capabilities. The batteries may be rechargeable batteries. The batteries may be lithium ion batteries, lithium polymer batteries, alkaline batteries or capacitors. In some embodiments, the stylus (201) has a stand-by battery time of at least 100 hours. In some embodiments, the stylus (201) has a data collection time of at least 24 hours.

In some embodiments, the stylus (201) may communicate with another medical device, or several devices, or equipment, such as an Implantable Pulse Generator used to treat Parkinson's disease or other portions of a Deep Brain Stimulation System. Such devices may be programmed by a clinician or patient programmer.

Figure 9:
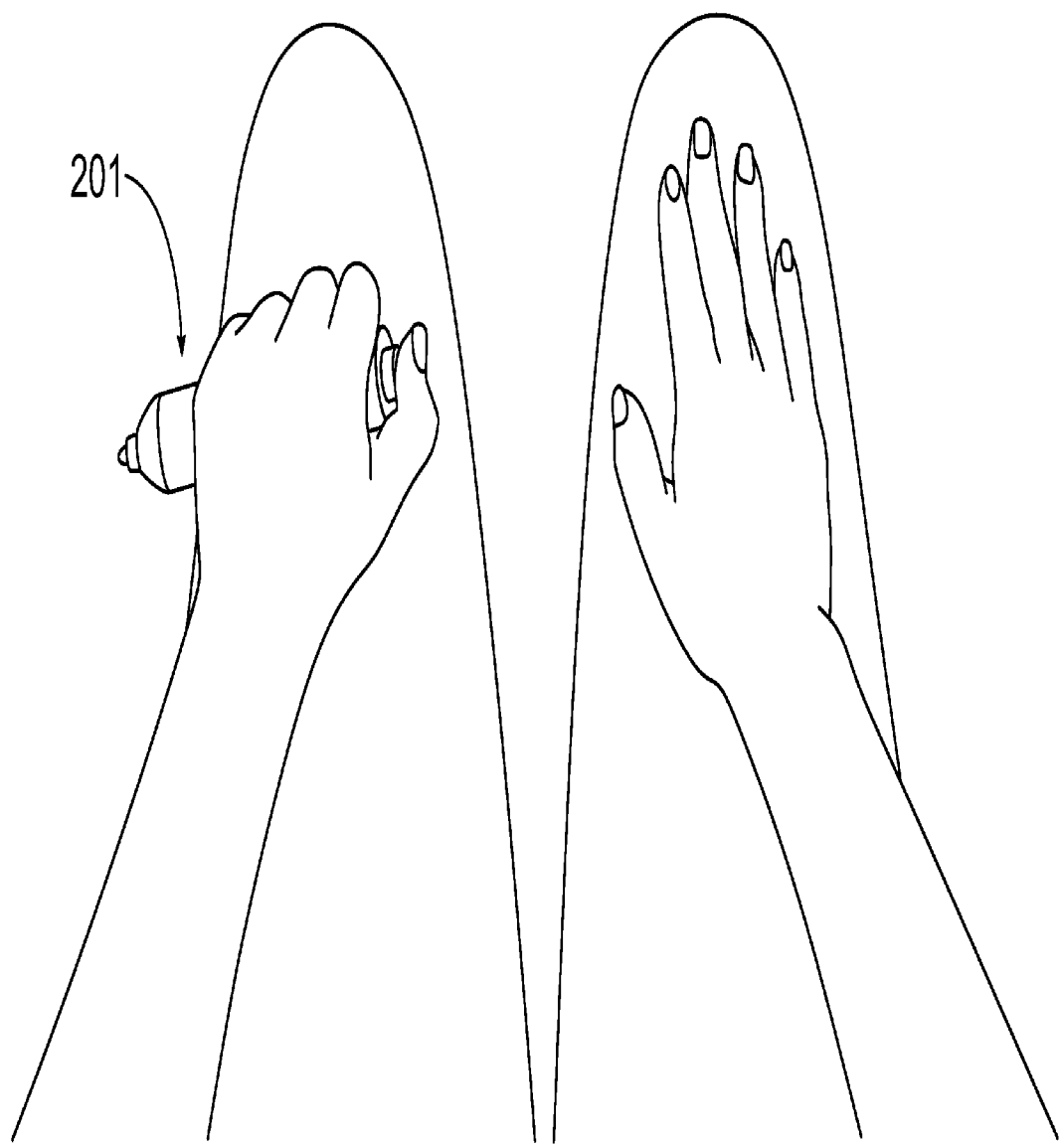
FIG. 9 depicts a user performing a task while holding an exemplary stylus in one hand, according to some embodiments of the present disclosure.
Figure 10:
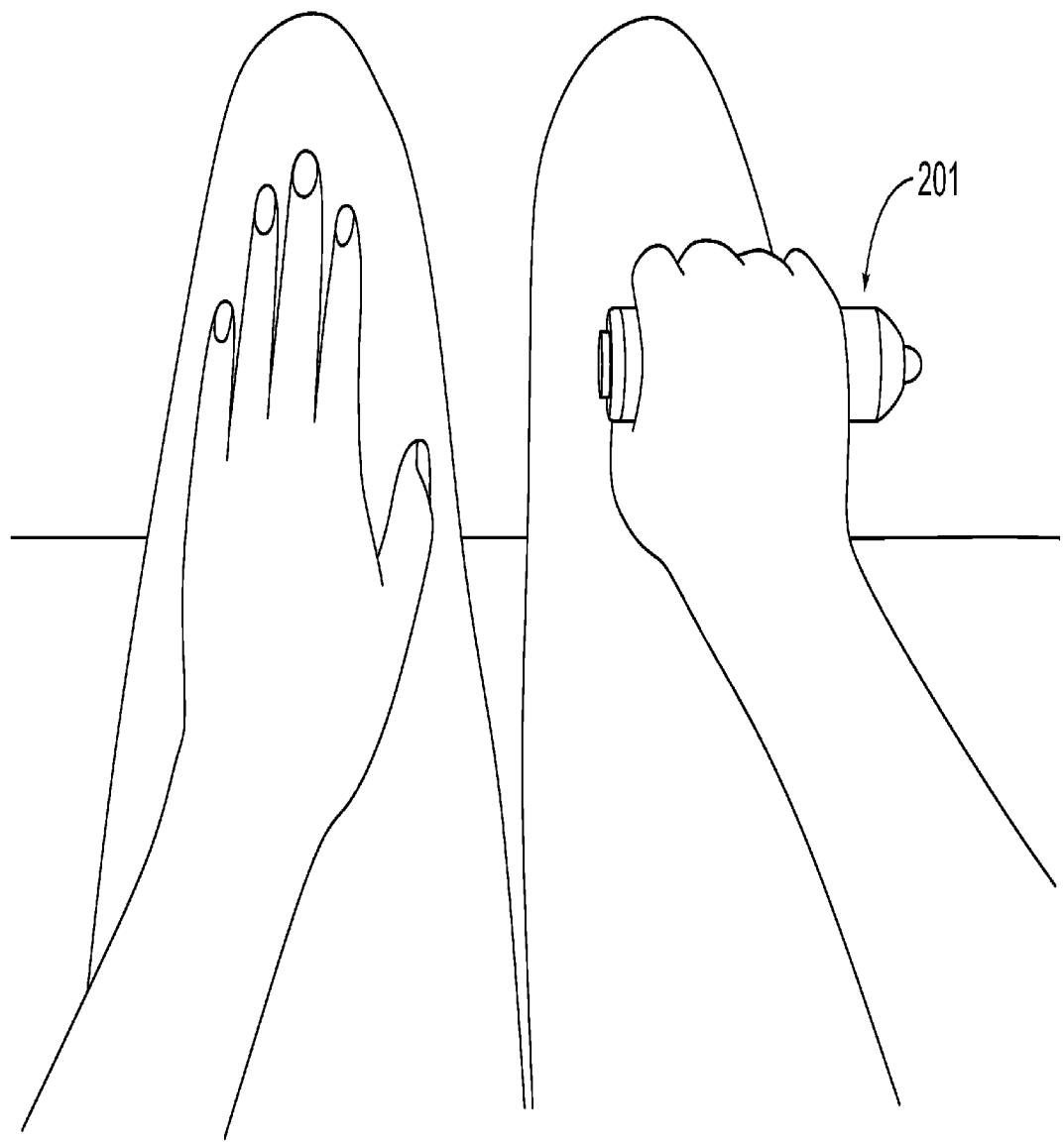
FIG. 10 depicts a user performing a task while holding an exemplary stylus in one hand, according to some embodiments of the present disclosure.

In some embodiments, the stylus (201) can be paired to an external computing device (301), such as a computer, a mobile device, or an external processor. A patient is instructed to perform one or more tasks or complete various assessments using the stylus (201). As illustrated in FIG. 9, an example task may instruct the patient to tap a target on the screen of a mobile device with the stylus tip (101), then to tap their chin with the stylus tip (101). During this task, the stylus (201) will stream or send the IMU sensor data and tip force data back to the external computing device (301), such as the mobile device, in real time. The IMU sensor data may be processed by the processor (401) to calculate rotational position in one or many planes, user acceleration in one or many planes, acceleration frequency power analysis in one or many planes. In some embodiments, the IMU sensor data and/or force data is stored in volatile or a non-volatile computer readable-medium within the stylus (201), and subsequently uploaded to an external computing device (301) or a cloud database. In certain embodiments, analysis of the data is completed by the processor (401) of the stylus (201). In some embodiments, analysis of the data is completed on the external computing device (301) or a cloud-based computing platform.

The stylus (201) has dimensions that allow usability and utility for a patient with a movement disorder. In certain embodiments, it is contemplated that the stylus (201) has a weight of less than 200 grams. In some embodiments, the stylus (201) has a weight of less than 150 grams. In some embodiments, the maximum diameter of the largest portion of the stylus body (102) is equal to or less than 30 millimeters. In some embodiments, the diameter of the largest portion of the stylus body (102) is equal to or less than 20 millimeters. In some embodiments, the stylus body (102) has an approximately uniform diameter. In certain embodiments, the length of the stylus body (102) is approximately 150 millimeters. In some embodiments, the length of the stylus body (102) is approximately 100 millimeters.

In certain embodiments, as shown in FIGS. 1-4, the stylus (201) has at least one button (105). In some embodiments, the button (105) is located at the proximal end of the stylus (201). In some embodiments, the button (105) is a multipurpose button to be used for a multitude of actions, including pairing the stylus (201) with a computing device, stopping or starting a timer during certain tasks, starting or stopping a test or assessment, or other operations. In some embodiments, the button (105) is used by the user for completing some tasks, such as pressing down the button (105) (see FIG. 9).

In some embodiments, the button (105) comprises a transparent or translucent material. In some embodiments, the button (105) contains a light. The light may have multiple modes and multiple colors that correspond with particular actions. In one embodiment, the light is green to indicate that data is being recorded or to indicate that the user is supposed to be performing an action. In some embodiments, the light is either neutral or off when no data is being recorded. Various colors of the light may be used to indicate different actions or states of the system, test, or device. In one example, a red light indicates at least one of the end of a test, a problem with pairing with a tablet, or a general system issue. In some embodiments, the button (105) contains a single light or a plurality of lights in a plurality of colors where the colors may or may not correspond to particular states of the system or actions to be performed. In some embodiments, upon activation or pressing of the button (105), the light changes its color, such as changing from green to red or from red to green, or changes its state from an on state to an off state, from an off state to an on state, or from one color state to another color state. In some embodiments, the light and the button are at different locations on the stylus (201). In some embodiments, one or more lights are located at a side or multiple sides of the body (102) or within the tip (101) of the stylus (201). In some embodiments, one or more lights are located on the base (202) instead of the stylus (201). In some embodiments, one or more lights are located on the base (202) in addition to the lights on the stylus (201).

In some embodiments, the button (105) has a tactile feel when pressed, providing the user feedback that the button has been pressed. In some embodiments, the button (105) has no travel but is a stationary surface with a force sensor such that when a force is applied to it, the stylus (201) changes from a first state to a secondary state. The tactile feel can be produced through any suitable mechanical or electrical devices, such as through a piezoelectric haptic feedback device. In general, multiple types of interactions with the stylus (201) can be performed with any of the types of buttons discussed above. Those interactions may include but are not limited to a single push, a plurality of pushes, a push and hold, a partial push, and a push for a specified amount of time.

Figure 13:
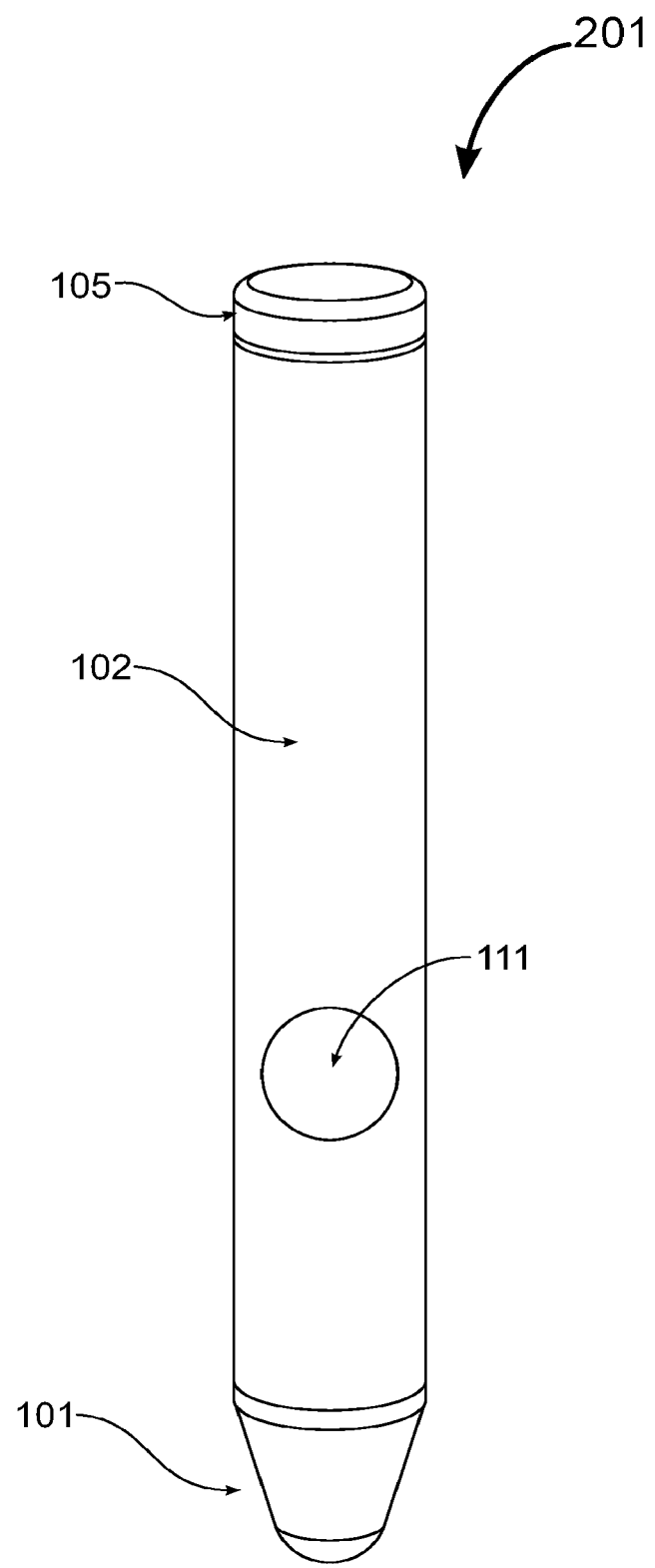
FIG. 13 depicts an exemplary stylus, according to some embodiments of the present disclosure.

FIG. 13 depicts an exemplary stylus, according to some embodiments of the present disclosure. In some embodiments, the one or more sides of the body (102) comprises a capacitive touch material configured to detect contact with a human hand. In some embodiments, as shown in FIG. 13, the stylus (201) includes one or more sensors (111) placed in one or more sides of the body (102). In some embodiments, the one or more sensors (111) comprise a capacitive touch material configured to detect contact with a human hand. In some embodiments, the one or more sensors (111) include one or more force sensors configured to obtain grip strength during some tests or as part of a test. In some embodiments, the one or more sensors (111) include one or more ultrasonic sensors configured to provide a fingertip or hand tracking capabilities during some tests or as part of a test.

In some embodiments, a device within the stylus (201) or the base (202) can produce an external stimulus to the user holding the stylus (201) to assess rigidity of the user. In some embodiments, the external stimulus is an external force or an electric current. The external force can be generated through a mechanical device, such as a falling mass, electromechanically induced movement of a mass, or a spring-loaded movement of a mass. In some embodiments, response to the external stimulus is monitored through the IMU of the stylus (201). In some embodiments, the external stimulus would have a pre-calibrated IMU response, which would be compared to the IMU response when the stylus (201) is being held by a user. The difference in the IMU response between the pre-calibrated external stimulus-only measurement, and the measurement made when the stylus (201) is being held by the user would serve as a measurement of rigidity of the user.

Figure 14:
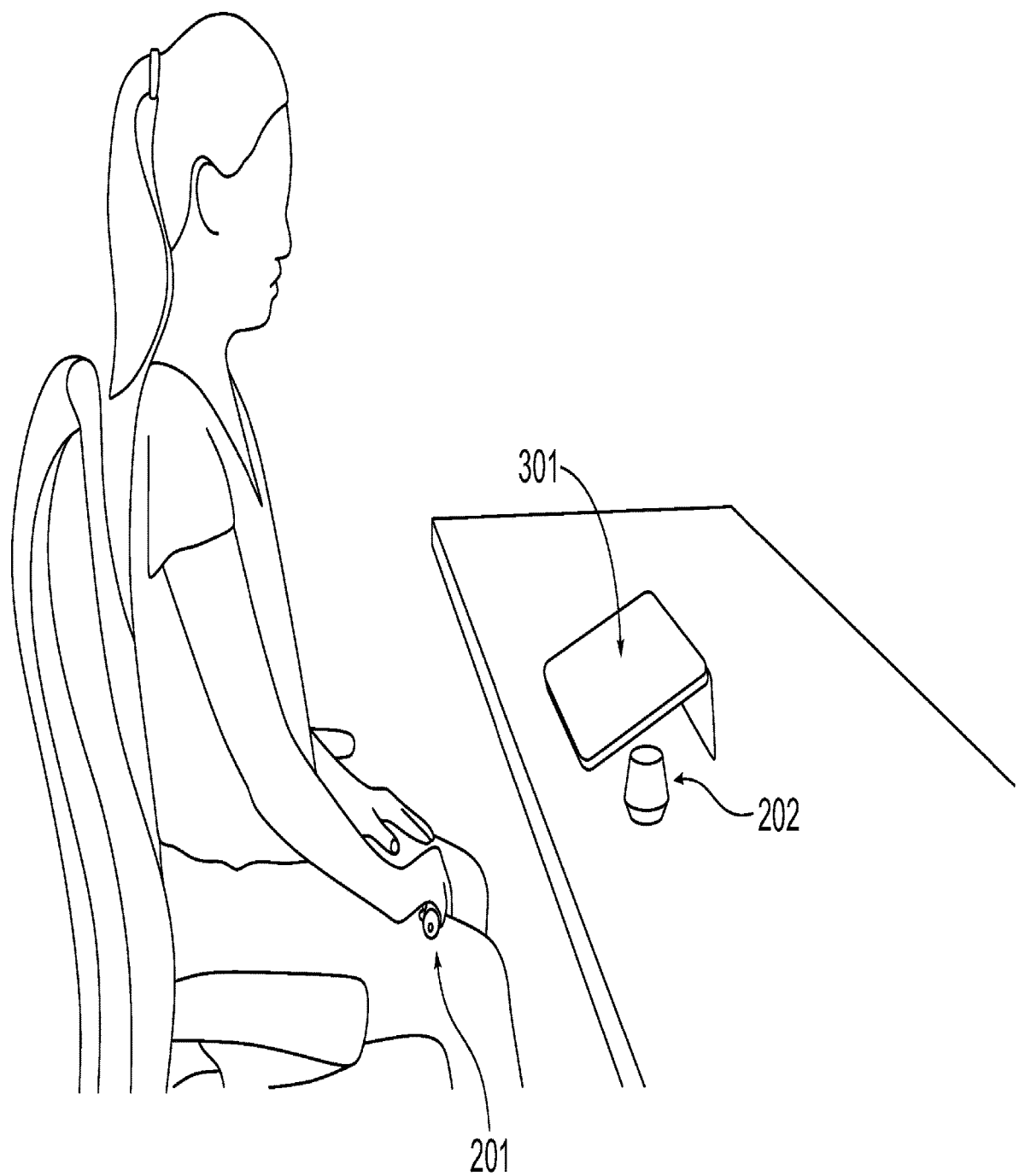
FIG. 14 depicts an exemplary base, an exemplary computing device, and a user holding an exemplary stylus in one hand, according to some embodiments of the present disclosure.
Figure 15:
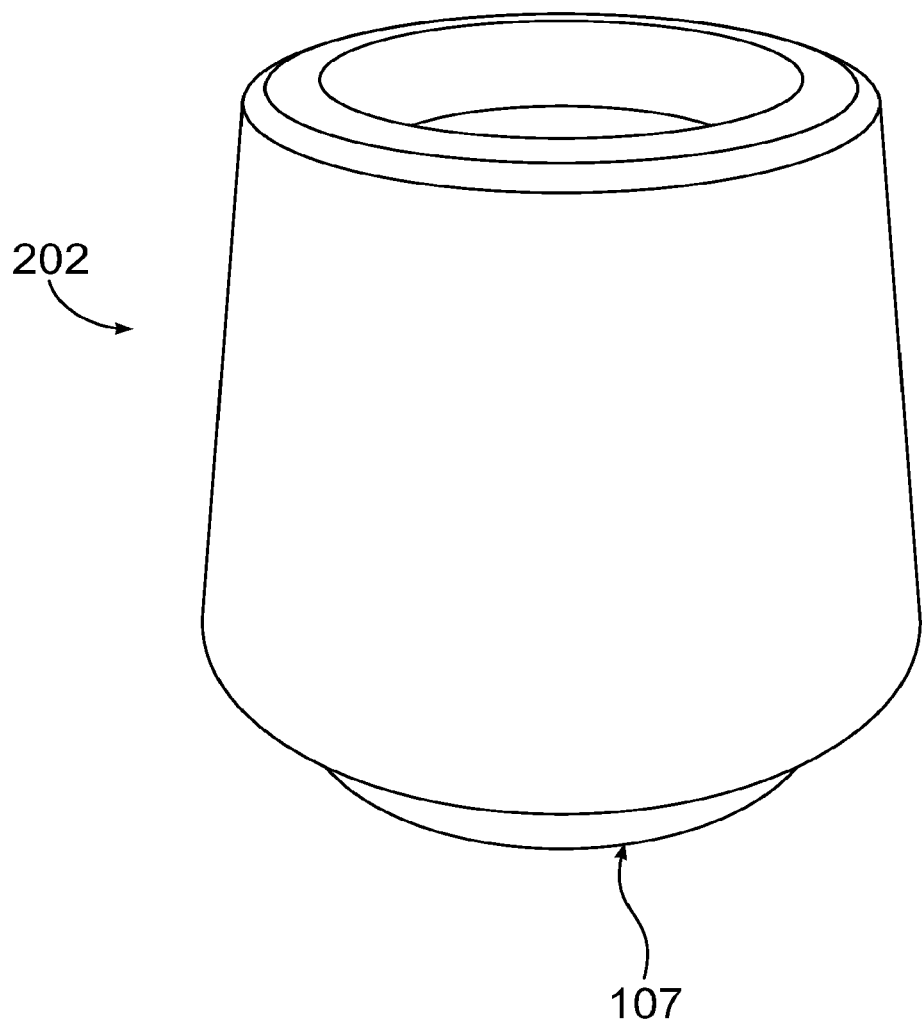
FIG. 15 depicts a front view of an exemplary base, according to some embodiments of the present disclosure.
Figure 16:
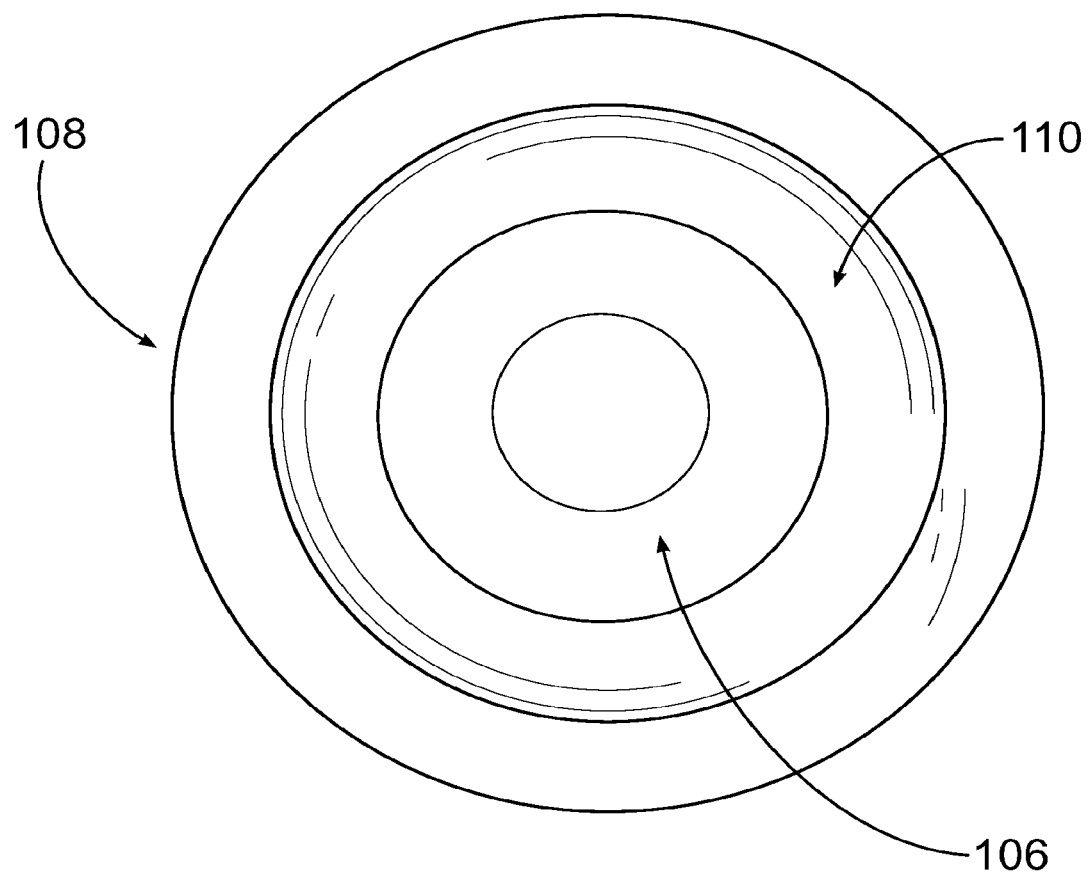
FIG. 16 depicts a top view of the exemplary base of FIG. 15.
Figure 17:
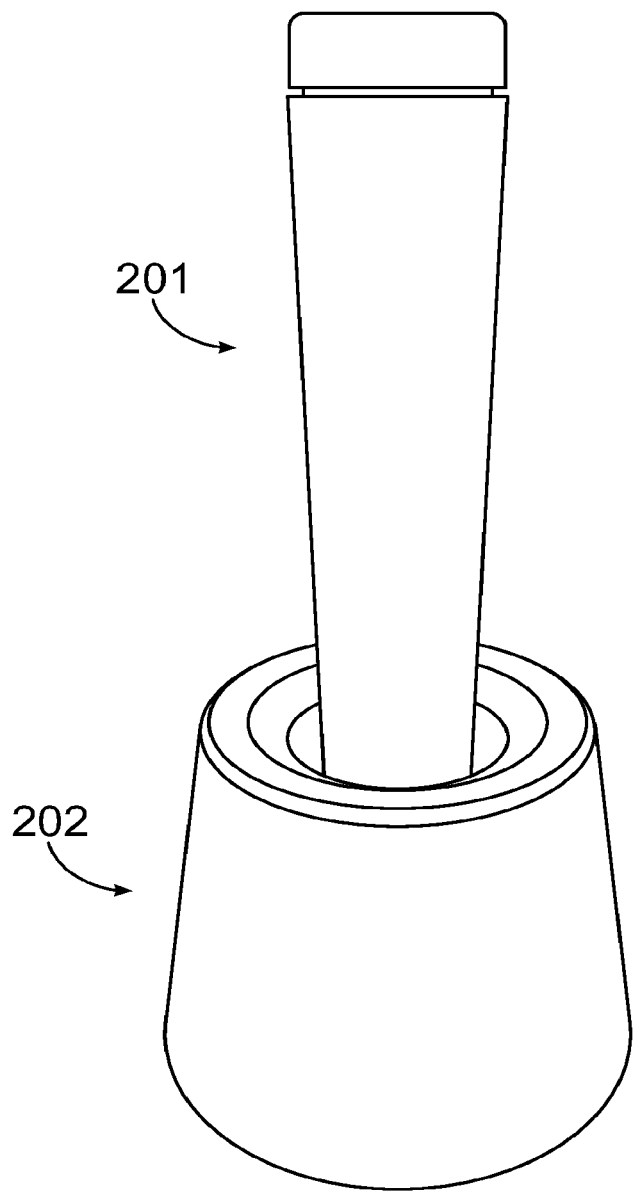
FIG. 17 depicts a front view of an exemplary stylus placed inside an exemplary base, according to some embodiments of the present disclosure.

According to some embodiments of the present disclosure, a base is provided. In some embodiments, the base includes one or more sensors. The one or more sensors include, but not limited to, an accelerometer, a gyroscope, a force sensor, or a magnetometer. In some embodiments, the base can be used similar to the stylus (201) for certain tests or assessments. FIG. 14 depicts an exemplary base (202), an exemplary computing device (301), and a user holding an exemplary stylus (201) in one hand, according to some embodiments of the present disclosure. FIG. 15 depicts a front view of an exemplary base (202) of an exemplary stylus, according to some embodiments of the present disclosure. FIG. 16 depicts a top view of the exemplary base of FIG. 15. FIG. 17 depicts a front view of an exemplary stylus (201) placed inside an exemplary base (202), according to some embodiments of the present disclosure.

As shown in FIGS. 15-17, in some embodiments, the base (202) includes a body having a cylindrical or a truncated cone shape with a flat bottom end (107). In some embodiments, the top of the base (202) has an aperture (106), forming a well within the base (202). In certain embodiments, the diameter of the aperture (106) decreases from a first diameter to a second diameter to form a cone-shaped or truncated-cone shaped internal surface (110) within the base (202). In some embodiments, the diameter of the aperture (106) is uniform from the opening of the aperture (106) to the bottom of the well. In some embodiments, the stylus (201) may be placed in the base (202) such that the internal surface (110) receives and holds at least a portion of the stylus (201). In certain embodiments, the stylus (201) is placed in the base (202) for storage.

In some embodiments, the base (202) includes at least one sensor configured to interact with the stylus (201). The at least one sensor may interact with the stylus (201), either while in contact or while not in contact with the stylus (201), to provide a positioning reference to the stylus indicating that either the stylus (201) is in base (202) or not. In some embodiments, the base (202) includes at least one battery. In some embodiments, the battery is a rechargeable battery. For example, the battery may be a lithium ion battery, a lithium polymer battery, or an alkaline battery, or a capacitor. In some embodiments, the base (202) includes a processor. In some embodiments, the processor includes a wireless communication module configured to wirelessly communicate with the stylus (201). In some embodiments, the base (202) includes a computer-readable storage medium configured to store data transmitted from the stylus (201). In certain embodiments, the base (202) includes a wireless charging circuit that allows for wirelessly charging the stylus (201). In some embodiments, the wireless charging circuit allows for charging the stylus (201) via contact between the base (202) and the stylus (201). In some embodiments, the wireless charging circuit allows for charging the stylus (201) without contact between the base (202) and the stylus (201). In some embodiments, the base (202) has a glossy finish on the internal surface (110). The glossy finish permits easier insertion of the stylus (201) into the aperture (106).

In certain embodiments, the base (202) contains at least one light. In some embodiments, the base (202) contains a plurality of lights that can be used as indicators such as but not limited to: start of a test, connection or pairing status of the stylus (201), charging status of the stylus (201), recording status of the stylus (201), whether a test is active or not. The light on the base (202) may be initiated or changed by actions on the stylus (201). In one example, the initial status of the light on the base (202) is orange, and the patient is directed to start a test by initiating the button (105) on the stylus (201). Upon initiation of the stylus button (105) and start of the test, the light on the base (202) turns green indicating that the test is ongoing.

According to some embodiments of the present disclosure, a system for assessing movement is provided. In some embodiments, the system allows for assessing the symptoms of a movement disorder or side effects of an intervention of movement disorders in a patient. In some embodiments, the system includes a stylus (201) and a computing device or a mobile device, such as a tablet, configured to have multiple mobile applications on it. In some embodiments, the system assesses a plurality of symptoms that are in different domains, such as motor symptoms, cognitive symptoms, or mood that may be caused by a disease or an intervention, such as pharmaceuticals or devices including Deep Brain Stimulation. In some embodiments, the symptoms can be assessed based on physiologic data measured through the system, such as tremor or other conditions. The measured physiological data can be assessed through the applications on the stylus (201), for example, by means of a test assessing tremor via the sensors of the stylus (201). Cognitive symptoms may be assessed via the computing device, such as the processing speed of an individual through a processing speed test. Other tests that may be performed by the system include but are not limited to walking speed, timed up-and-go, visual memory, patient reported surveys or outcomes, trail making test, postural tremor, resting tremor, postural stability, bradykinesia, grip strength, manual dexterity, vision, rigidity, speech, emergent tremor, and others.

The stylus and/or system provided by the present disclosure can also assess patients with other conditions that would require a plurality of assessments in different domains of symptoms. The conditions may include but not limited to autism, heart failure, heart disease, stroke, traumatic brain injury, vestibular disease, migraines, dementia, ALS, and attention deficit disorder (ADD).

Interventions for movement disorders can have positive effects on symptoms, such as tremor, and can also cause side effects, such as cognitive issues. Titration of pharmaceuticals or stimulation parameters during deep brain stimulation can be difficult given all the different parameters and domains that need to be assessed as well as the number of potential therapeutic options, such as stimulation settings, that are available.

According to some embodiments of the present disclosure, a method of titrating treatment for a patient with a movement disorder is provided. In some embodiments, one or more assessments of a patient is performed by the patient using the stylus and system consistent with embodiments of the present disclosure. In some embodiments, the one or more assessments include, but not limited to, tremor, postural stability, timed up and go, processing speed test, and various assessments of a patient's movement or motor function. In some embodiments, based on the one or more assessments, a first set of an Effect Score and a Side Effect Score are calculated via an algorithm by the computing device, such as a mobile device, the stylus, or the base. In some embodiments, based on the one or more assessments, a performance score is calculated via an algorithm by the computing device, such as a mobile device, the stylus, or the base. In some embodiments, a treatment or a treatment plan will be given to the patient based on at least one of the Effect Score, the Side Effect Score, and the performance score. In some embodiments, the treatment includes at least one of a pharmaceutical, pharmacological, physical therapy, exercise, or stimulation intervention. In some embodiments, the stimulation intervention is generated by a stimulation device. In some embodiments, the dose of the treatment will be entered into the computing device, such as an iPad. In some embodiments, the stylus will suggest an alternative treatment plan for the patient. In some embodiments, the patient will be given a different treatment, such as different stimulation parameters or a different dose of a treatment.

In some embodiments, after an appropriate washout period to allow for the old treatment to stop and the new treatment to take place, the assessments will be performed again by the patient. Based on the assessments performed again by the patient, a second set of the Effect Score and Side Effect Score will be calculated. In some embodiments, the first set of scores will be compared with the second set of scores in order to make a treatment decision, such as about the medication, dose, or stimulation. In some embodiments, the stylus and/or the system will suggest one of: the original parameters, the second parameters, or new parameters to test. This process can be completed a plurality of times over a duration of time. The duration of time may include time intervals and durations of a day, a week, a month, several months, or one or more years to titrate the patient's treatment. Given the fact that many neurologic diseases are degenerative, assessments may need to be performed periodically throughout the life of the patient. In some embodiments, the starting point will be with an initial treatment. In some embodiments, the initial treatment will be assessed by comparing a patient's score or scores on a first task or a first set of tasks with that patient's score or scores on a second task or a second set of tasks. In some embodiments, the starting point will be with no treatment.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. Moreover, while illustrative embodiments have been described herein, the scope of the disclosure includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive.

It is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as exemplary only, with a true scope and spirit of the disclosed embodiments being indicated by the following claims

What is claimed is:

1. A system for assessing movement, the system comprising:

a handheld device comprising
a plurality of sensors configured to record motion and position data,
a body having a plurality of sides,
a battery, and
a proximal end configured to interact with a touchscreen of a computing device; and
a base comprising a body with a flat bottom end and a top end, the base being separated from a computing device with which the handheld device interacts, the base having an inner surface configured to engagingly couple at least a portion of the body of the handheld device.

2. The system of claim 1, wherein the base comprises at least one sensor configured to interact with the handheld device and a computer-readable storage medium configured to store data transmitted from the handheld device.

3. The system of claim 1, wherein the base comprises a wireless charging circuit configured to wirelessly charge the handheld device.

4. The system of claim 1, wherein the plurality of sensors comprises an accelerometer, a gyroscope, and a magnetometer.

5. The system of claim 1, wherein the handheld device comprises a button at a distal end, the button being capable of being depressed by a patient from a first position to a second position and returning to the first position when released by the patient.

6. The system of claim 5, wherein the button contains one or more lights.

7. The system of claim 5, wherein the button provides tactile feedback to a patient when depressed to the second position.

8. The system of claim 1, wherein the plurality of sides is an odd number.

9. The system of claim 1, wherein the body of the base has an outer surface with a first diameter;
wherein the top end has an aperture with a second diameter smaller than the first diameter of the outer surface; and
wherein the cone-shaped inner surface has a third diameter at the top end and a fourth diameter at the flat bottom end.

10. The system of claim 9, wherein the cone-shaped inner surface comprises a glossy finish.

11. The system of claim 9, wherein the contact between the base and the handheld device causes wireless charging of the handheld device.

12. The system of claim 1, wherein the handheld device further comprises a computer-readable storage medium configured to store the motion and position data and a processor configured to process the motion and position data.

13. The system of claim 1, wherein the handheld device comprises a communication module configured to wirelessly transmit the stored and processed motion and position data to an external computing device.

14. The system of claim 1, wherein the plurality of sides comprise a capacitive touch material configured to detect contact with a human hand.

15. The system of claim 1, wherein the movement comprises at least one of essential tremor, Parkinson's disease, ataxia, dystonia, Parkinsonism, or tremor.

16. The system of claim 1, wherein the stylus provides tactile feedback to a patient during an assessment.

17. A method of assessing movement, the method comprising:
administering a pre-determined task to a patient using a handheld device, at least a portion of which is engagingly coupled in a base,
the handheld device comprising
a plurality of sensors configured to record motion and position data,
a body comprising a plurality of sides,
a battery, and
a proximal end configured to interact with a touchscreen of a computing device; and
the base being separate from a computing device with which the handheld device is configured to interact;
recording motion and position data from the handheld device during the predetermined task; and
placing the handheld device into the base receptable following the predetermined task.

18. The method of claim 17, further comprising transmitting data from the handheld device to the computing device;
calculating, by the computing device, a performance score using an algorithm and data received from the handheld device;
outputting, by the computing device, the performance score; and
determining, by the computing device, a treatment for the patient using the performance score.

19. The method of claim 18, wherein the treatment comprises a pharmaceutical, pharmacological, exercise, or stimulation intervention.

* * * * *